(12) United States Patent
Dejima et al.

(10) Patent No.: US 8,439,828 B2
(45) Date of Patent: May 14, 2013

(54) TREATMENT ENDOSCOPE

(75) Inventors: Takumi Dejima, Tokyo (JP); Kiyotaka Matsuno, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 1313 days.

(21) Appl. No.: 12/127,449

(22) Filed: May 27, 2008

(65) Prior Publication Data

US 2009/0036736 A1    Feb. 5, 2009

Related U.S. Application Data

(63) Continuation-in-part of application No. 12/057,990, filed on Mar. 28, 2008, which is a continuation-in-part of application No. 12/035,535, filed on Feb. 22, 2008, which is a continuation-in-part of application No. 11/809,488, filed on Jun. 1, 2007, now Pat. No. 8,021,293, which is a continuation-in-part of application No. 11/652,880, filed on Jan. 12, 2007, which is a continuation-in-part of application No. 11/435,183, filed on May 16, 2006, which is a continuation-in-part of application No. 11/331,963, filed on Jan. 13, 2006, now Pat. No. 8,092,371.

(51) Int. Cl.
*A61B 1/00*    (2006.01)

(52) U.S. Cl.
USPC ............ 600/146; 600/104; 600/106; 600/114

(58) Field of Classification Search .................. 600/104, 600/106, 139–142, 146–152, 107, 114–116; 606/1; 604/523–528
See application file for complete search history.

(56) References Cited

U.S. PATENT DOCUMENTS

| 4,245,624 A | 1/1981 | Komiya |
| 4,577,621 A | 3/1986 | Patel |

(Continued)

FOREIGN PATENT DOCUMENTS

| CN | 1602166 A | 3/2005 |
| CN | 1886087 A | 12/2006 |

(Continued)

OTHER PUBLICATIONS

U.S. Office Action dated Oct. 5, 2011 from corresponding U.S. Appl. No. 11/652,880.

(Continued)

*Primary Examiner* — Matthew J Kasztejna
*Assistant Examiner* — Ryan Henderson
(74) *Attorney, Agent, or Firm* — Scully Scotty Murphy & Presser, PC

(57) ABSTRACT

In a treatment endoscope which includes: an elongated insertion section having a first channel for inserting a treatment instrument therethrough; an arm, having a second channel for inserting a treatment instrument therethrough, attached to the distal end of the insertion section so that the first channel communicates with the second channel; a first operation section for operating the arm; and a second operation section for operating the insertion section, the arm has a first bending section which can be operated to be bent via the first operation section, the insertion section has a second bending section which can be operated to be bent via the second operation section, and an interlock mechanism connects the first operation section to the second operation section so that, when either one of the first bending section and the second bending section is bent by operating either one of the first operation section and the second operation section, the other one of the first bending section and the second bending section bends.

2 Claims, 14 Drawing Sheets

U.S. PATENT DOCUMENTS

| | | | |
|---|---|---|---|
| 4,873,965 | A | 10/1989 | Danieli |
| 5,173,716 | A | 12/1992 | Tetsuka |
| 5,299,559 | A | 4/1994 | Bruce et al. |
| 5,318,013 | A | 6/1994 | Wilk |
| 5,395,367 | A | 3/1995 | Wilk |
| 5,448,989 | A | 9/1995 | Heckele |
| 5,683,349 | A | 11/1997 | Makower et al. |
| 5,855,569 | A | 1/1999 | Komi |
| 5,916,147 | A | 6/1999 | Boury |
| 5,976,075 | A | 11/1999 | Beane et al. |
| 6,013,024 | A | 1/2000 | Mitsuda et al. |
| 6,352,503 | B1 | 3/2002 | Matsui et al. |
| 6,780,151 | B2 | 8/2004 | Grabover et al. |
| 7,833,156 | B2 | 11/2010 | Williams et al. |
| 2002/0087048 | A1 | 7/2002 | Brock et al. |
| 2004/0044270 | A1 | 3/2004 | Barry |
| 2004/0117032 | A1 | 6/2004 | Roth |
| 2004/0138525 | A1 | 7/2004 | Saadat et al. |
| 2004/0138529 | A1 | 7/2004 | Wiltshire et al. |
| 2004/0193212 | A1 | 9/2004 | Taniguchi et al. |
| 2005/0065397 | A1 | 3/2005 | Saadat et al. |
| 2005/0075538 | A1 | 4/2005 | Banik et al. |
| 2005/0090709 | A1* | 4/2005 | Okada et al. ............ 600/104 |
| 2005/0119522 | A1 | 6/2005 | Okada |
| 2005/0222495 | A1 | 10/2005 | Okada et al. |
| 2005/0228224 | A1 | 10/2005 | Okada et al. |
| 2005/0234294 | A1 | 10/2005 | Saadat et al. |
| 2005/0234296 | A1 | 10/2005 | Saadat et al. |
| 2005/0250989 | A1 | 11/2005 | Suzuki et al. |
| 2005/0273085 | A1* | 12/2005 | Hinman et al. ............ 606/1 |
| 2006/0111615 | A1 | 5/2006 | Danitz et al. |
| 2006/0189845 | A1 | 8/2006 | Maahs et al. |
| 2007/0004967 | A1 | 1/2007 | Ueno et al. |
| 2007/0043338 | A1 | 2/2007 | Moll et al. |
| 2007/0156019 | A1 | 7/2007 | Larkin et al. |
| 2007/0167679 | A1 | 7/2007 | Miyamoto et al. |
| 2007/0167680 | A1 | 7/2007 | Miyamoto et al. |
| 2007/0232856 | A1 | 10/2007 | Ueno et al. |
| 2007/0270640 | A1 | 11/2007 | Dimitriou et al. |
| 2007/0299387 | A1 | 12/2007 | Williams et al. |
| 2008/0051631 | A1 | 2/2008 | Dejima et al. |
| 2008/0065109 | A1 | 3/2008 | Larkin |
| 2008/0221391 | A1 | 9/2008 | Weitzner et al. |

FOREIGN PATENT DOCUMENTS

| | | | |
|---|---|---|---|
| EP | 1 872 709 A1 | 1/2008 | |
| EP | 1 967 123 A1 | 9/2008 | |
| JP | 55-45436 | 3/1980 | |
| JP | 56-104501 | 8/1981 | |
| JP | 63-102401 | 7/1988 | |
| JP | S63-242217 | 10/1988 | |
| JP | 5-5105 U | 1/1993 | |
| JP | 5-49594 | 3/1993 | |
| JP | 8-131441 | 5/1996 | |
| JP | 10-258022 | 9/1998 | |
| JP | 11-318815 A | 11/1999 | |
| JP | 2001-46393 A | 2/2001 | |
| JP | 2002-253563 A | 9/2002 | |
| JP | 2004-180781 | 7/2004 | |
| JP | 2004-290569 | 10/2004 | |
| JP | 2005-287963 | 10/2005 | |
| JP | 2005-296412 | 10/2005 | |
| JP | 2006-141624 | 6/2006 | |
| JP | 2006-516910 | 7/2006 | |
| JP | 2006-516910 A | 7/2006 | |
| JP | 2007-151595 | 6/2007 | |
| JP | 2007-175070 | 7/2007 | |
| JP | 2007-275624 A | 10/2007 | |
| WO | WO 2004/064600 A2 | 8/2004 | |
| WO | WO 2007/057880 A2 | 5/2007 | |
| WO | WO 2007/074571 A1 | 7/2007 | |
| WO | WO 2007/080974 A1 | 7/2007 | |
| WO | WO 2007/127199 A1 | 11/2007 | |

OTHER PUBLICATIONS

U.S. Office Action dated Jul. 9, 2010.

U.S. Office Action dated Feb. 1, 2011 received in related U.S. Appl. No. 11/809,488.

U.S. Office Action dated Mar. 24, 2010, received in related U.S. Appl. No. 11/435,183.

U.S. Office Action dated Mar. 2, 2011 received in related U.S. Appl. No. 11/652,880.

U.S. Office Action dated Mar. 16, 2011 received in related U.S. Appl. No. 11/435,183.

U.S. Office Action dated Nov. 30, 2011 of related U.S. Appl. No. 12/057,990.

Office Action dated May 15, 2012 received in related U.S. Appl. No. 11/652,880.

U.S. Office Action mailed May 31, 2012 in related U.S. Appl. No. 12/024,704.

U.S. Office Action mailed Jun. 26, 2012 in related U.S. Appl. No. 12/058,029.

U.S. Office Action mailed Jul. 2, 2012 in related U.S. Appl. No. 12/057,990.

U.S. Office Action mailed Jul. 3, 2012 in related U.S. Appl. No. 12/035,535.

Chinese Office Action dated Jul. 3, 2012 from related Chinese Patent Application Publication No. 2007-80008372.7, together with an English language translation.

U.S. Office Action dated Mar. 28, 2012 of related U.S. Appl. No. 13/212,610.

Japanese Office Action dated Feb. 19, 2013 together with an English Translation issued in corresponding Japanese Application No. 2009-058066.

Japanese Office Action (Notice of Reasons for Rejection) dated Dec. 18, 2012 from corresponding Japanese Patent Application Publication No. JP 2009-013615, together with an English language translation.

Japanese Office Action (Notice of Reasons for Rejection) dated Dec. 18, 2012 from corresponding Japanese Patent Application Publication No. JP 2009-027835, together with an English language translation.

Japanese Office Action (Notice of Reasons for Rejection) dated Dec. 18, 2012 from corresponding Japanese Patent Application Publication No. JP 2009-033278, together with an English language translation.

Notice of Allowance dated Jan. 22, 2013 issued in corresponding U.S. Appl. No. 11/652,880.

U.S. Final Office Action dated Mar. 19, 2013 issued in corresponding U.S. Appl. No. 12/058,029.

* cited by examiner

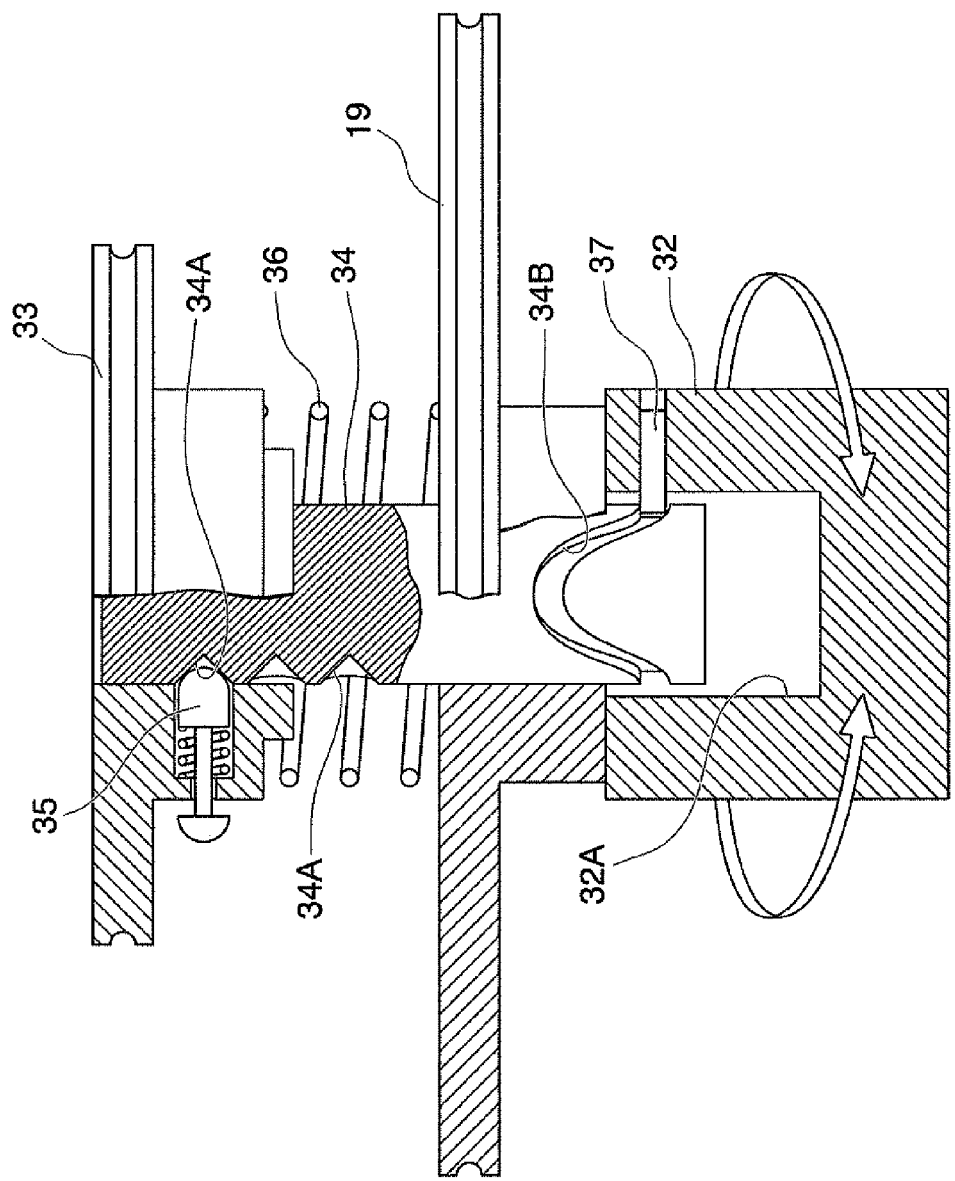

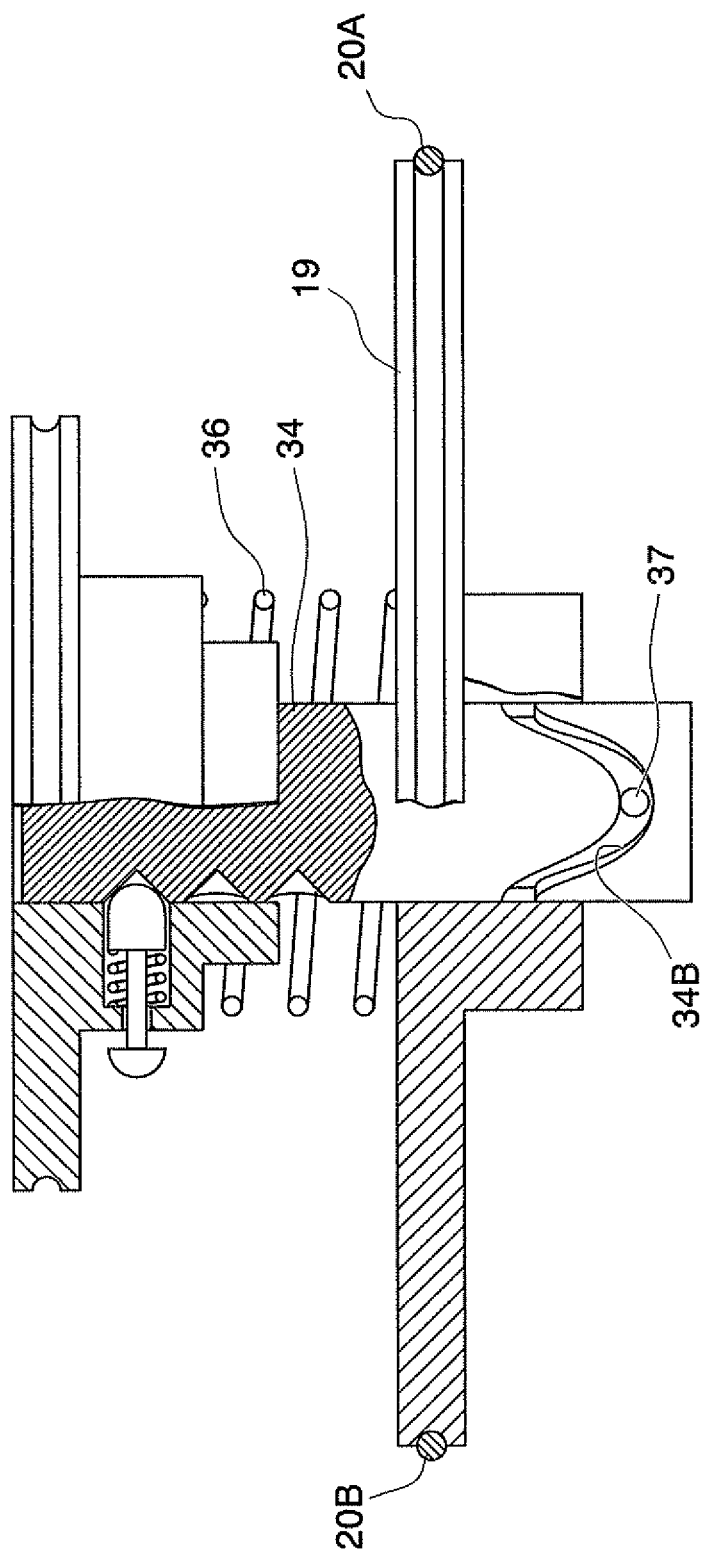

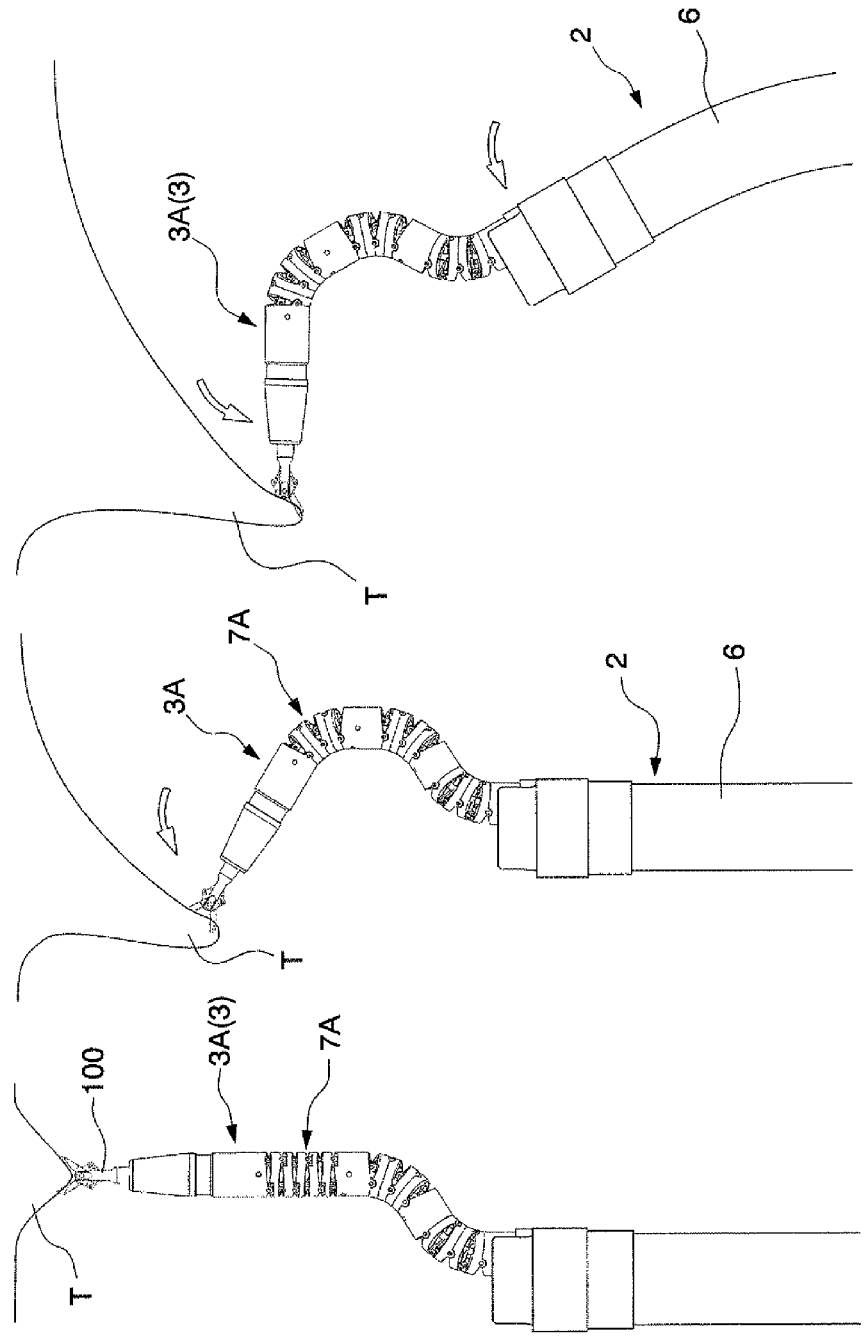

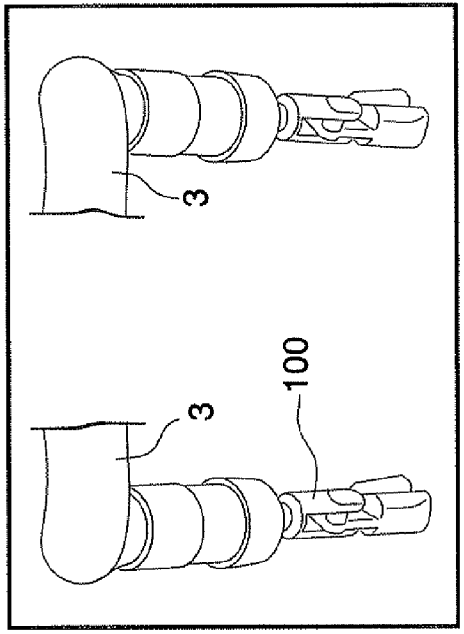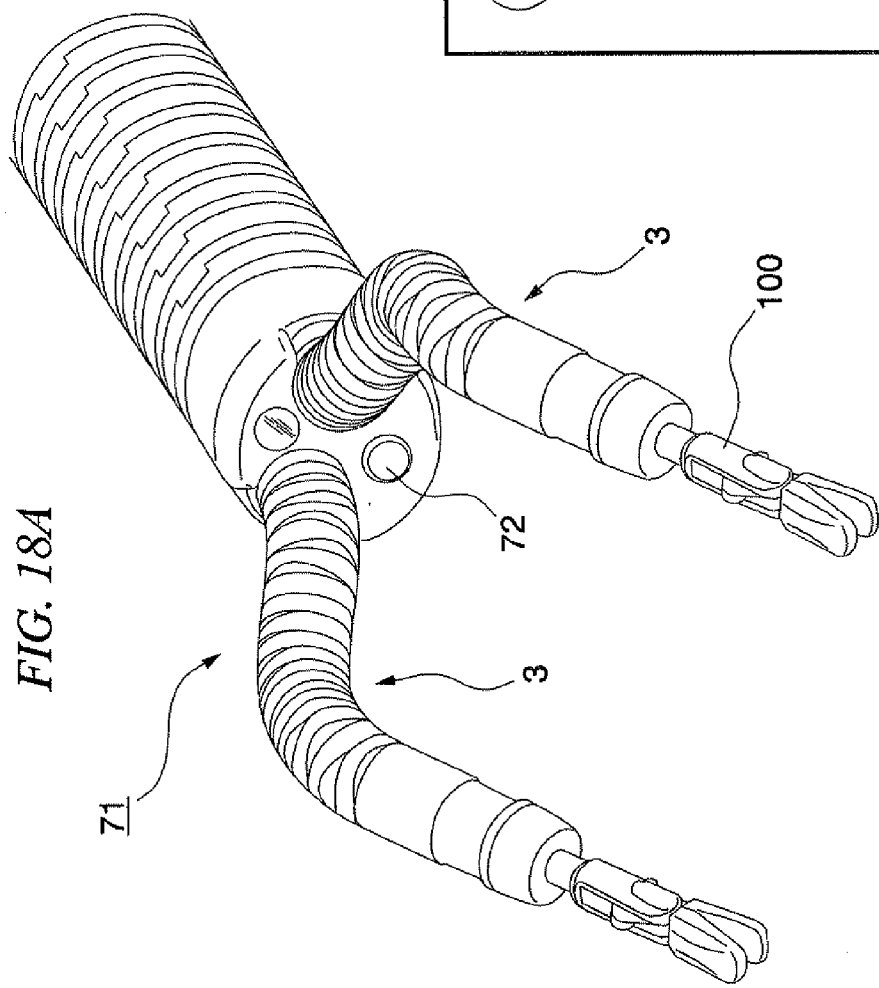

TREATMENT ENDOSCOPE

CROSS REFERENCE TO RELATED APPLICATIONS

This is a Continuation In-part Application (CIP) based on U.S. patent application Ser. No. 12/057,990, titled "MEDICAL APPARATUS", filed Mar. 28, 2008, which is a CIP based on U.S. patent application Ser. No. 12/035,535, titled "MEDICAL TREATMENT ENDOSCOPE", filed Feb. 22, 2008, which is a CIP based on U.S. patent application Ser. No. 11/809,488, titled "MEDICAL TREATMENT ENDOSCOPE", filed Jun. 1, 2007 now U.S. Pat. No. 8,021,293, which is a CIP based on U.S. patent application Ser. No. 11/652,880, titled "MEDICAL TREATMENT ENDOSCOPE", filed Jan. 12, 2007, which is a CIP based on U.S. patent application Ser. No. 11/435,183, titled "MEDICAL TREATMENT ENDOSCOPE", filed May 16, 2006, which is a CIP based on U.S. patent application Ser. No. 11/331,963, titled "MEDICAL TREATMENT ENDOSCOPE", filed Jan. 13, 2006 now U.S. Pat. No. 8,092,371.

BACKGROUND OF THE INVENTION

1. Field of the Invention

The present invention relates to a treatment endoscope having a treatment instrument inserted into an arm section which is provided at the distal end of an insertion section and operated to conduct treatment.

2. Background Art

Laparoscopic surgery is a known technique for conducting medical activities including observation of or treatment for the organs of human body, and this technique provides manipulation by making a plurality of openings on the gastric wall and inserting a treatment instrument such as laparoscopy or forceps, etc. into each opening instead of making a large abdominal incision. This type of surgery is advantageous because the mere formation of small openings on the gastric wall can reduce stress imposed on a patient.

As a method of even further reducing stress on the patient, it has been proposed in recent years to carry out manipulations by inserting a flexible endoscope into the patient via a natural opening such as the mouth, nostrils or anus. An example of a medical treatment endoscope used in such procedures is disclosed in U.S. Patent Application Publication No. 2005/0065397.

In the medical treatment endoscope disclosed in this reference, arm members that have a bendable end are respectively inserted into a plurality of lumens disposed within a flexible inserted part that is inserted into the body via the mouth of the patient. By inserting respective instruments through these arm members, the procedure site can be approached from different directions with the various instruments. Accordingly, a plurality of procedures can be carried out in continuum by means of a single endoscope inserted into the body.

SUMMARY OF THE INVENTION

A first aspect of the present invention is a treatment endoscope which includes: an elongated insertion section having a first channel for inserting a treatment instrument therethrough; an arm, having a second channel for inserting a treatment instrument therethrough, attached to the distal end of the insertion section so that the first channel communicates with the second channel; a first operation section for operating the arm; and a second operation section for operating the insertion section, so that the arm has a first bending section which can be operated to be bent via the first operation section, the insertion section has a second bending section which can be operated to be bent via the second operation section, and an interlock mechanism connects the first operation section to the second operation section so that, when either one of the first bending section and the second bending section is bent by operating either one of the first operation section and the second operation section, the other one of the first bending section and the second bending section bends.

BRIEF DESCRIPTION OF DRAWINGS

FIG. 5 shows a first operation shaft of the treatment endoscope according to a second embodiment of the present invention in a fragmentary sectional view.

FIG. 6 shows the initial state of the first operation shaft.

FIG. 7 shows the movement of the arm section of the treatment endoscope when used.

FIG. 8 shows the movement of the arm section of the treatment endoscope when used.

FIG. 9 shows the movement of the arm section of the treatment endoscope when used.

FIG. 18A is an isometric view of a modified example of the distal end of the insertion section of the treatment endoscope according to the present invention.

FIG. 18B shows a visual field of an observation device of the treatment endoscope.

PREFERRED EMBODIMENTS

Figure 1:
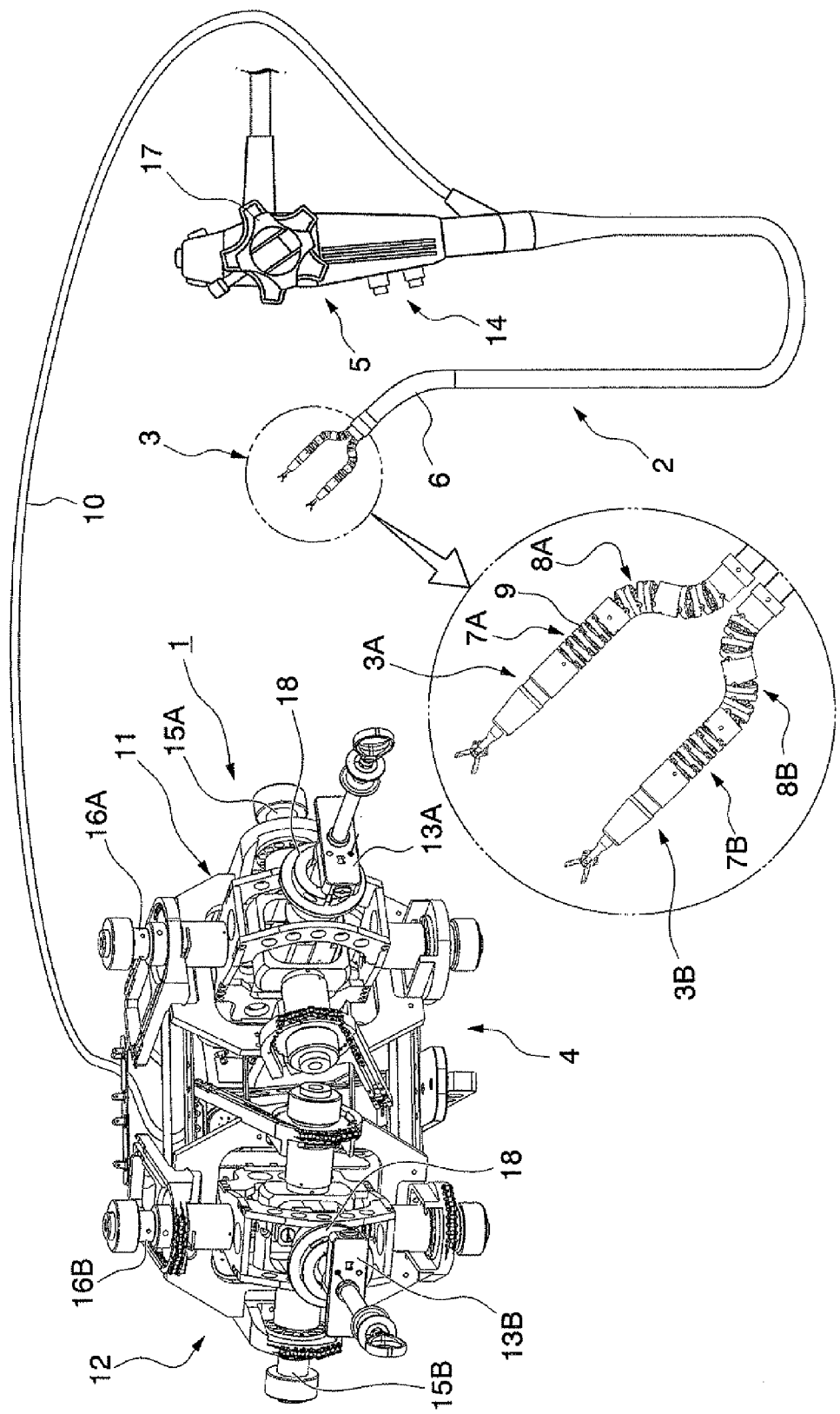
FIG. 1 shows the configuration of a treatment endoscope according to a first embodiment of the present invention.

A first embodiment of the present invention will be explained as follows with reference to FIGS. 1 to 4. FIG. 1 shows the configuration of a treatment endoscope 1 according to the present embodiment.

The treatment endoscope 1 includes an insertion section 2 inserted into a body cavity; an arm section 3 provided at the distal end of the insertion section 2; a first operation section 4 for operating the arm section 3; and a second operation section 5 for operating the insertion section 2.

The flexible and elongated insertion section 2 has an operation channel (first channel), not shown in drawings, for inserting a treatment instrument therethrough. The insertion section 2 has a bending section (second bending section) 6 having a commonly known structure. A plurality of substantially cylindrical connected joint rings, not shown in the drawings, are aligned in an axial line direction. In addition, wires (transmission members), not shown in the drawings, facing with each other and having the axial line of the joint rings therebetween are inserted into the joint rings and attached thereto. Operating the second operation section 5 allows the wires connected to the second operation section 5 to bend a bending section 6. An observation device, not shown in the drawings, attached to the distal end of the insertion section 2 and movable distally and proximally in a predetermined range permits observation of, for example, a treatment site in the body cavity or of the arm section 3.

The arm section 3 has two arms 3A and 3B each having a channel (second channel) which allows a treatment instrument to pass therethrough. Each channel of the arms 3A and 3B communicates with the operation channel of the insertion section 2.

The arms 3A and 3B have first bending sections 7A and 7B and second bending sections 8A and 8B. The second bending sections 8A and 8B are provided proximally relative to the first bending sections 7A and 7B.

A plurality of substantially cylindrical joint rings 9 aligned in an axial line direction are connected to the first bending sections 7A and 7B similarly to the bending section 6. In addition, two pairs of two wires (transmission members), not shown in the drawings, facing each other and having the axial line of the joint rings 9 therebetween are attached so that the phase of the two pairs of wires is shifted by 90 degrees on the joint rings 9. Operating appropriately, i.e., retracting the four wires connected to the first operation section 4 appropriately allows the arms 3A and 3B to bend in four directions. It should be noted that two directions of the four directions are parallel with a plane defined by the arms 3A and 3B and parallel with one of swinging directions of the bending section 6. This direction indicates the "horizontal direction" in the following explanations.

The second bending sections 8A and 8B are mechanisms capable of bending and fixing to facilitate operation, which will be explained later, of the treatment instruments inserted through the arms 3A and 3B so that the distance of the axial lines of the arms 3A and 3B attached substantially in parallel increases more significantly than the distance shown in FIG. 1. Substantially similar to the first bending sections 7A and 7B, each of the second bending sections 8A and 8B is provided with joint rings and wires. The second bending sections 8A and 8B can be bent and fixed by retracting the wires. The wires extending from the first bending sections 7A and 7B and the second bending sections 8A and 8B further extend to the first operation section 4 through the link sheath 10.

The first operation section 4 for operating the arms 3A and 3B of the arm section 3 is provided with a first operation unit 11 for operating the arm 3A and a second operation unit 12 for operating the arm 3B.

Operation sticks 13A and 13B operated by a user are attached to the operation units 11 and 12 respectively. The operating sticks 13A and 13B which have the same structure have a channel for inserting the treatment instrument therethrough. Each channel is connected to a forceps port 14 provided in the vicinity of the proximal end of the insertion section 2 through, for example, a tube not shown in the drawings, and communicates with the operation channel, not shown in the drawings, in the insertion section 2.

The operation sticks 13A and 13B has first operation shafts 15A, and 15B and second operation shafts 16A and 16B, respectively attached thereto. The first operation shafts 15A and 15B make rotation interlocked with vertical operation conducted by using the operation sticks 13A and 13B. The second operation shafts 16A and 16B make rotation interlocked with horizontal operation conducted by using the operation sticks 13A and 13B. The wires extending through the link sheath 10 for operating the first bending sections 7A and 7B are attached to the first operation shafts 15A and 15B, and to the second operation shafts 16A and 16B of the operation units 11 and 12 respectively. In addition, the wire, not shown in the drawings, for operating the second bending sections 8A and 8B are connected to a slider 18 provided to each of the operation sticks 13A and 13B. The wires can be retracted by drawing the slider 18 proximally.

The second operation section 5 has an angle knob 17. The bending section 6 can be bent by operation to rotate the angle knob 17.

Figure 2:
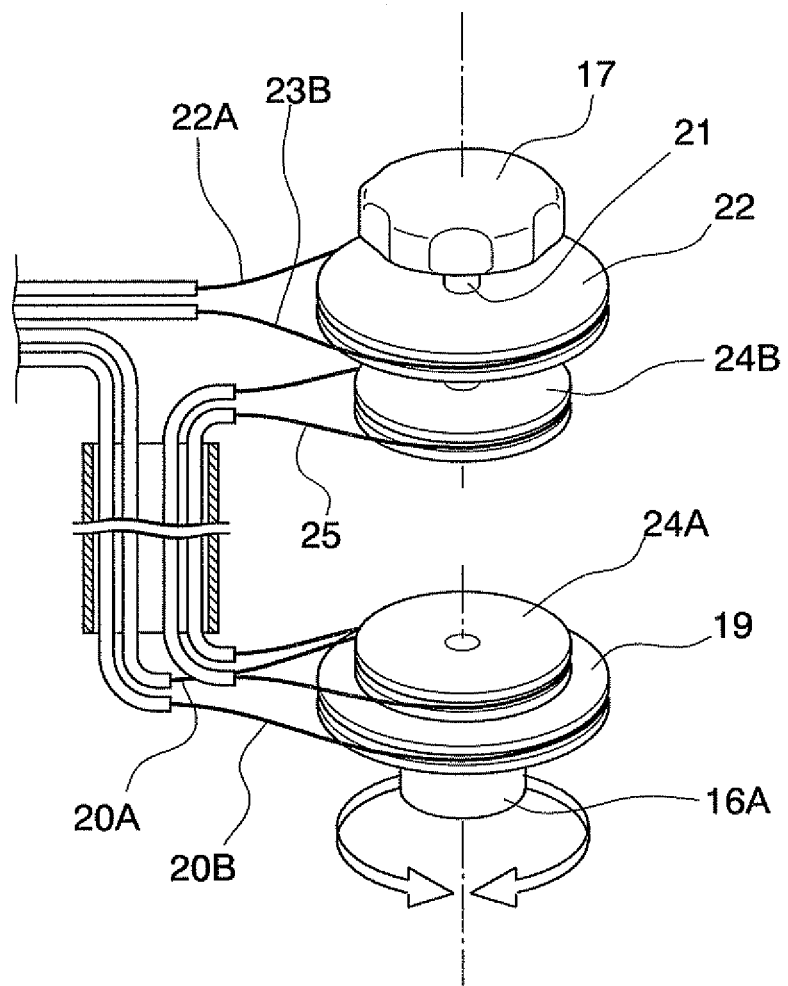
FIG. 2 shows the structure of transmitting the endoscope's operation.

FIG. 2 shows the structure of transmitting the operation of the treatment endoscope 1. A pulley (first operation member) 19 is attached to the second operation shafts 16A and 16B coaxially, of the first operation section 4 (FIG. 2 shows only the second operation shaft 16A). The proximal ends of a pair of wires 20A and 20B connected to the first bending section 7A are connected to the outer periphery of the pulley 19. In addition, a pulley (second operation member) 22 is attached coaxially to a third operation shaft 21 having the angle knob 17 of the second operation section 5 attached thereto. A pair of wires 23A and 23B connected to the bending section 6 are connected to the outer periphery of the pulley 22.

Link pulleys 24A and 24B are attached to the second operation shaft 16A and the third operation shaft 21 respectively and coaxially. The link pulleys 24A and 24B are connected by a link wire 25. Therefore, rotational operation of one of the second operation shaft 16A and the third operation shaft 21 causes the link pulleys 24A and 24B and the link wire 25 to be operable as a interlock mechanism, and the other one is interlocked and rotated in the same direction.

Operations in using the treatment endoscope 1 having the previously explained configuration will be explained.

In the beginning, a user inserts the insertion section 2 of the treatment endoscope 1 into the body cavity of for example, a patient. During the insertion, the inserted state of second bending sections 8A and 8B of the arms 3A and 3B of the arm section 3 is not bent, i.e., the second bending sections 8A and 8B are maintained in a substantial straight line. Each wire for operating the arm section 3 and the insertion section 2 can be inserted smoothly since the connected wires having slack in some degree can follow the serpentine path, etc. in the body cavity flexibly.

Upon reaching the arm section 3 to the vicinity of a treatment object tissue, the user inserts treatment instruments used with the operation sticks 13A and 13B of the first operation section 4, and projects the treatment instruments from the distal ends of the arm section 3 through the channels of the insertion section 2. Subsequently, drawing the sliders 18 of the operation sticks proximally, that is, toward the handling side causes the wires connected to the second bending sections 8A and 8B to be retracted, thereby bending the arms 3A and 3B and fixing so that the distance of the axial lines of the arms 3A and 3B increases as shown in FIG. 1.

The user conducts manipulation by moving the operation sticks 13A and 13B vertically and horizontally while observing the object tissue and the arm section 3 with an observation device, and moving the arms 3A and 3B each having the treatment instrument projecting therefrom into desirable directions.

Figure 4:
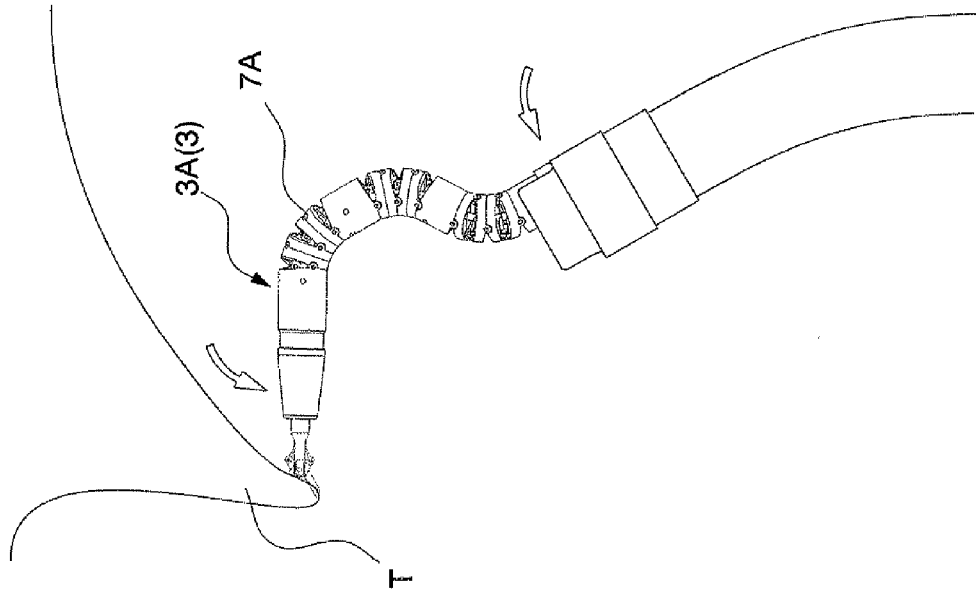
FIG. 4 shows the movement of an arm section of the endoscope when used.
Figure 3:
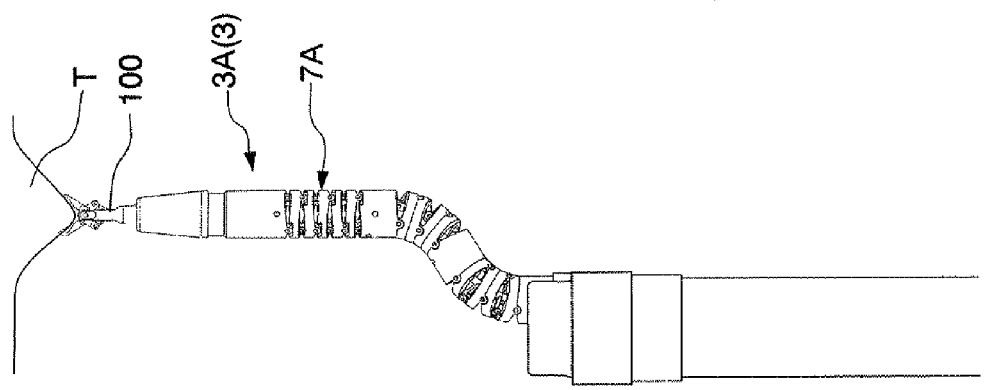
FIG. 3 shows the movement of an arm section of the treatment endoscope when used.

FIG. 3 shows an operation of retracting an object tissue T with the arm section 3. The drawing shows only the right-hand side of arm 3A to render the drawing more legible. In the event that the user grasps the object tissue T with the distal ends of a treatment instrument 100 and retracts the grasped object tissue T in a left-hand direction in FIG. 3, the operation stick 13A attached to the first operation unit 11 of the first operation section 4 is rotated in a counterclockwise direction. Subsequently, the second operation shaft 16A is rotated and the wires connected to the first bending section 7A are retracted, and accordingly, the first bending section 7A of the arm 3A bends in the left-hand direction as shown in FIG. 4. The link pulley 24A attached to the second operation shaft 16A rotates in the same direction in accordance with the bending of the first bending section 7A. The movement of the link pulley 24A is also transferred to the link pulley 24B attached to the second operation section 5 through the link wire 25. This causes the pulley 22 of the second operation section 5 to rotate and causes the wires connected to the bending section 6 to be retracted, thereby causing the bending section 6 to bend in the same direction as that of the first bending section 7A as shown in FIG. 4.

The reaction force produced by retracting the tissue T acts on the first bending section 7A and the bending section 6 of the insertion section 2. Therefore, in some case using a conventional treatment endoscope, it is difficult to retract the tissue T significantly because the bending sections failing to endure the reaction force inevitably bend in the direction opposite the first bending section (the right-hand direction in this case). However, according to the treatment endoscope 1 of the present embodiment, the bending section 6 of the insertion section 2 interlocked with the first bending section and bending in the same direction can endure the bending caused by the reaction force. Therefore, the treatment object tissue can be retracted with a significant force because the insertion section 2 endures the reaction force produced by retracting the insertion section 2

A second embodiment of the present invention will be explained next with reference to FIGS. 5 to 11. A treatment endoscope 31 according to the present embodiment is different from the previously explained treatment endoscope 1 because a first operation section and a second operation section are interlocked when a predetermined degree of operation is provided. It should be noted that configurations that are equivalent to those of the previously explained first embodiment will be assigned the same numeric symbol and redundant explanation thereof will be omitted.

FIG. 5 shows a second operation shaft 32 of the treatment endoscope 31 in fragmentary sectional view. The second operation shaft 32 is fixed to the pulley 19 for operating the first bending section of an arm coaxially and unitarily. A link shaft 34 having a link pulley 33 attached thereto is inserted into the pulley 19 rotatably and further inserted into a recession section 32A provided in the second operation shaft 32.

A plurality of substantial cylindrical grooves 34A are formed on the outer periphery of the link shaft 34. A pin 35 urged to project in the axial line thereof is provided in the link pulley 33. The link pulley 33 is locked to the link shaft 34 by fitting the pin 35 into the grooves 34A.

A spring 36 placed between the pulley 19 and the link pulley 33 urges the pulley 19 and the link pulley 33 so that the distance therebetween increases.

A cam groove 34B is formed on the outer periphery in the vicinity of the lower end of the link shaft 34. In addition, a pin 37 attached to the second operation shaft 32 and projecting into the recession section 32A engages with the cam groove 34B. The pin 37 and the cam groove 34B are adjusted so that the pin 37 engages with the cam groove 34B at the position most close to the lower end of the link shaft 34 in the initial state, i.e. in the straight state of the first bending section of an arm as shown in FIG. 6.

Operation of the treatment endoscope 31 having the previously explained configuration will be explained with reference to an example using the arm 3A.

In the event of retraction, etc. of the tissue T, the user in the beginning grasps the object tissue T with the distal ends of the treatment instrument 100 projecting from the arm 3A as shown in FIG. 7. Subsequently, the first bending section 7A is bent by rotating or moving the operation stick 13A.

The link pulley 33 in this state does not start movement linked with the pulley 19 because the spring separates the pulley 19 of the second operation shaft 32 from the link pulley 33. However, when the second operation shaft 32 is rotated by rotating or moving the operation stick 13A, the pin 37 attached to the second operation shaft 32 upon making contact with the oblique surface of the cam groove 34B of the link shaft 34 moves in the cam groove 34B so that the pin 37 approaches the link pulley 33 gradually. Accordingly the link shaft 34 resisting the urging force of the spring 36 moves downward gradually, and then, the link pulley 33 approaches the pulley 19. In this process, only the arm 3A bends as shown in FIG. 8 while the bending section 6 of the insertion section 2 does not start to bend yet.

Figure 10:
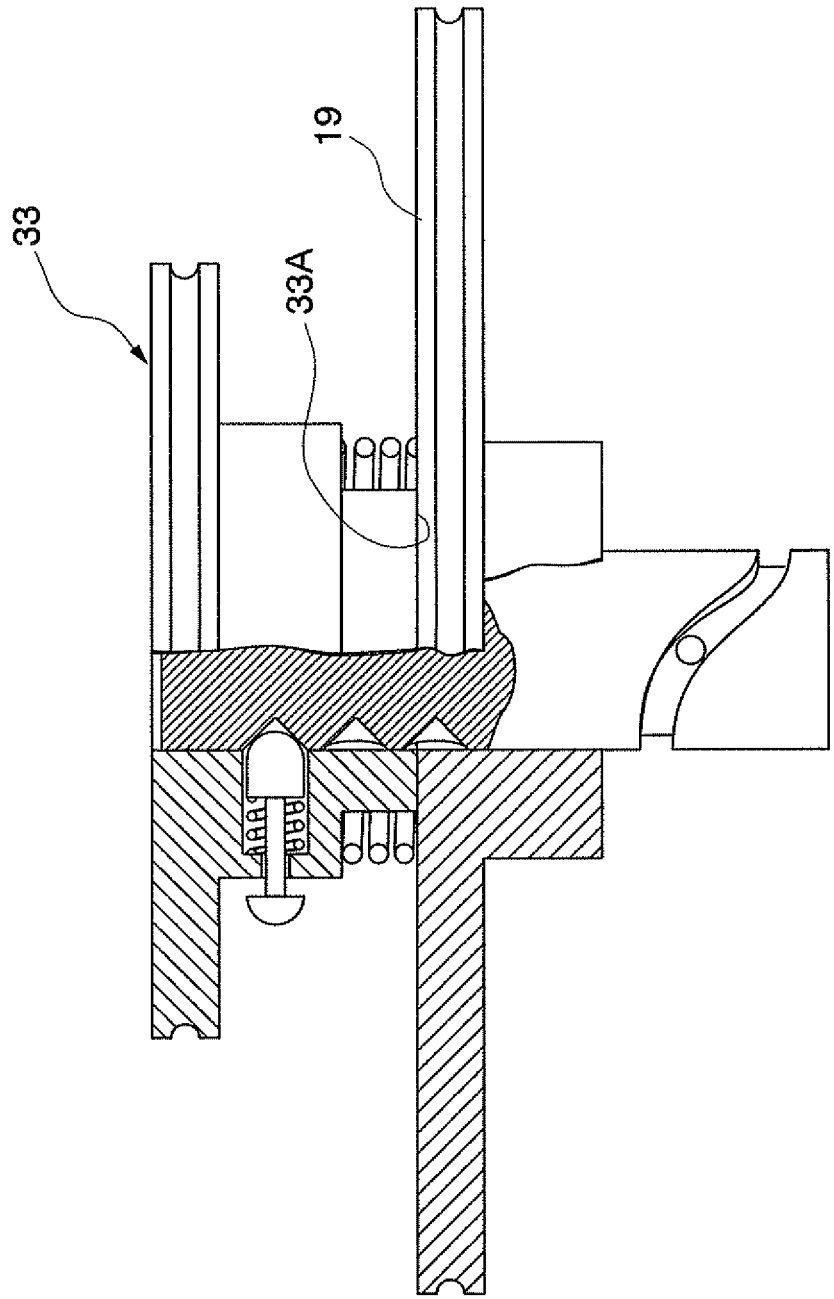
FIG. 10 illustrates the first operation shaft when linked movement is started.

Further rotating or moving the operation stick 13A causes a bottom surface 33A of the link pulley 33 to make contact with the pulley 19 as shown in FIG. 10. Subsequently, the pulley 19 is fixed to the link pulley 33 by the mutual friction force, and then, the pulley 19 and the link pulley 33 rotate in one unit. After this point in time, the first bending section 7A starts moving linked with the bending section 6 of the insertion section 2, and the bending section 6 of the insertion section 2 bends in addition to the bending of the arm 3A as shown in FIG. 9; therefore, the shape of the insertion section 2 is maintained, and a retractive operation with a more significant stroke can be conducted.

The timing of starting the movement of the pulley 19 linked with the link pulley 33 can be adjusted within a fixed range by changing the clearance between the pulley 19 and the link pulley 33. The user, in an attempt to change the clearance, may change the position of the pin 35 engaging with the grooves 34A of the link shaft 34 by operating the pin 35 of the link pulley 33. That is, the pin 35 and the grooves 34A are operable as an adjusting mechanism for adjusting the operation degree which is necessary for the linked movement.

The treatment endoscope 31 according to the present embodiment can obtain the same effect as that of the treatment endoscope 1 according to the first embodiment. Also, a more desirably operable treatment endoscope can be configured by adjusting so that a relatively small bending operation, for example, a mere tissue grasping operation or a dissectional operation does not make a linked movement, and so that the bending section 6 of the insertion section 2 moves to link with the movement of the first bending section of the arm section 3 in a relatively large bending operation, for example, tissue retraction, because one of the operation sections 4 and 5 must be operated by at least a constant degree until the bending section 6 and the first bending section start linked movement.

In place of the aforementioned embodiment which has been explained with reference to the example in which the arm section makes movement linked with the bending section by at least a fixed operation degree irrespective of the bending direction, a treatment endoscope may be configured so that the bending movement of the arm section linked with the bending section is limited in an arbitrary direction. The following is an example.

Figure 11:
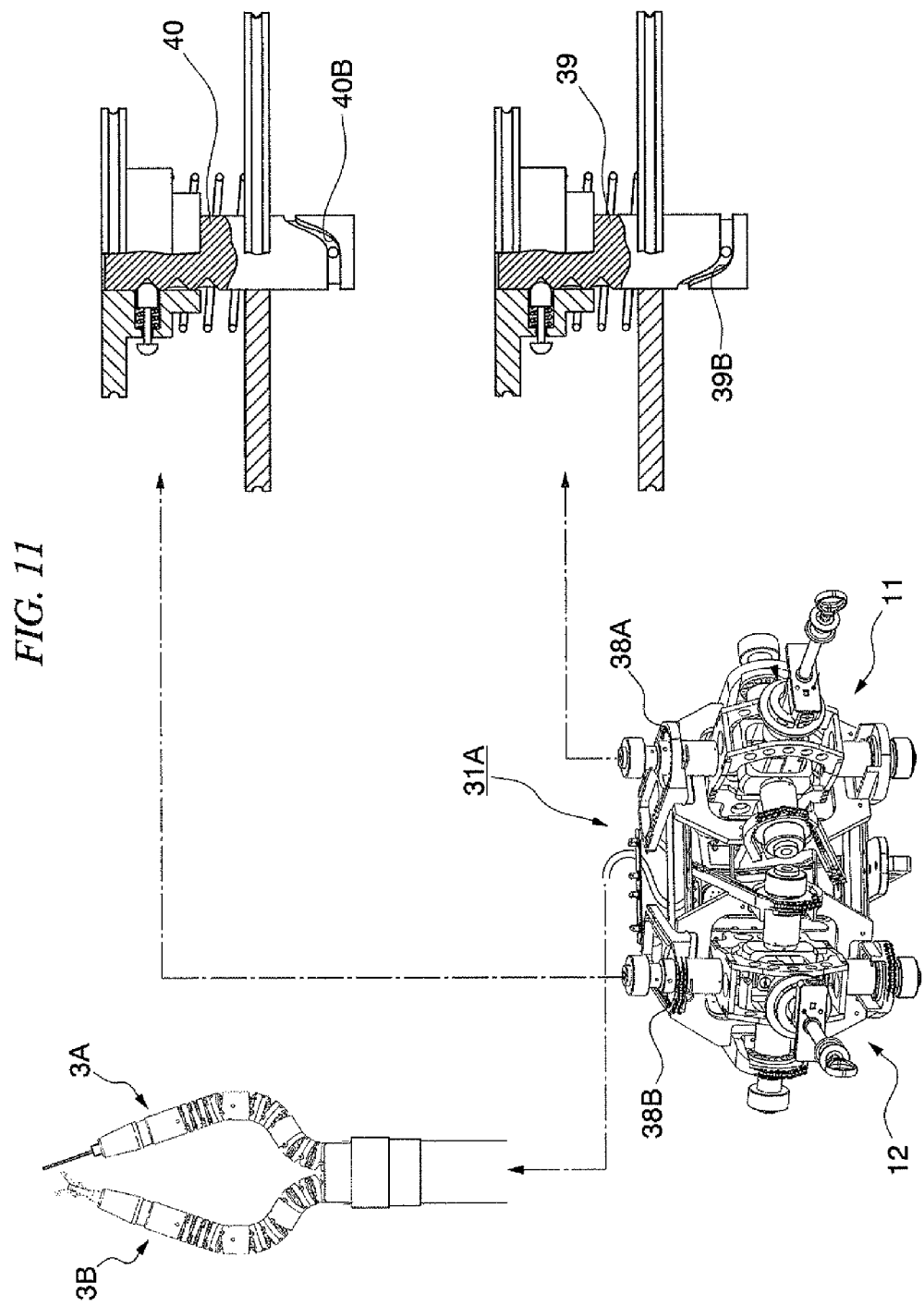
FIG. 11 is a view showing a modified example of treatment endoscope according to the embodiment.

FIG. 11 shows a treatment endoscope 31A as a modified example of the present embodiment. When viewed from the proximal end, an oblique surface is provided on a left-hand region of a cam groove 39B of a link shaft 39 inserted into a second operation shaft 38A of the first operation unit 11 for operating the arm 3A shown on the right-hand side of the drawing. On the other hand, when viewed from the proximal end, an oblique surface is provided on a right-hand region of a cam groove 40B of a link shaft 40 inserted into a second operation shaft 38B of the second operation unit 12 for operating the arm 3A shown on the left-hand side of the drawing.

Therefore, the bending section 6 of the insertion section 2 makes linked movement only when the right-hand arm 3A bends in right-hand directions and only when the left-hand arm 3B bends in left-hand directions. An interlock mechanism having the aforementioned configuration can achieve the object desirably since, in many cases operations, e.g., retraction which needs interlocked movement, are conducted while one arm is bent and separate from the other arm.

Next, a third embodiment of the present invention will be explained with reference to FIGS. 12 to 17. The treatment endoscope of the present embodiment is different from the treatment endoscope 1 according to the aforementioned first embodiment based on the structure of a first operation section. It should be noted that configurations that are equivalent to those of the previously explained first embodiment will be assigned the same numeric symbol and redundant explanations thereof will be omitted.

Figure 12:
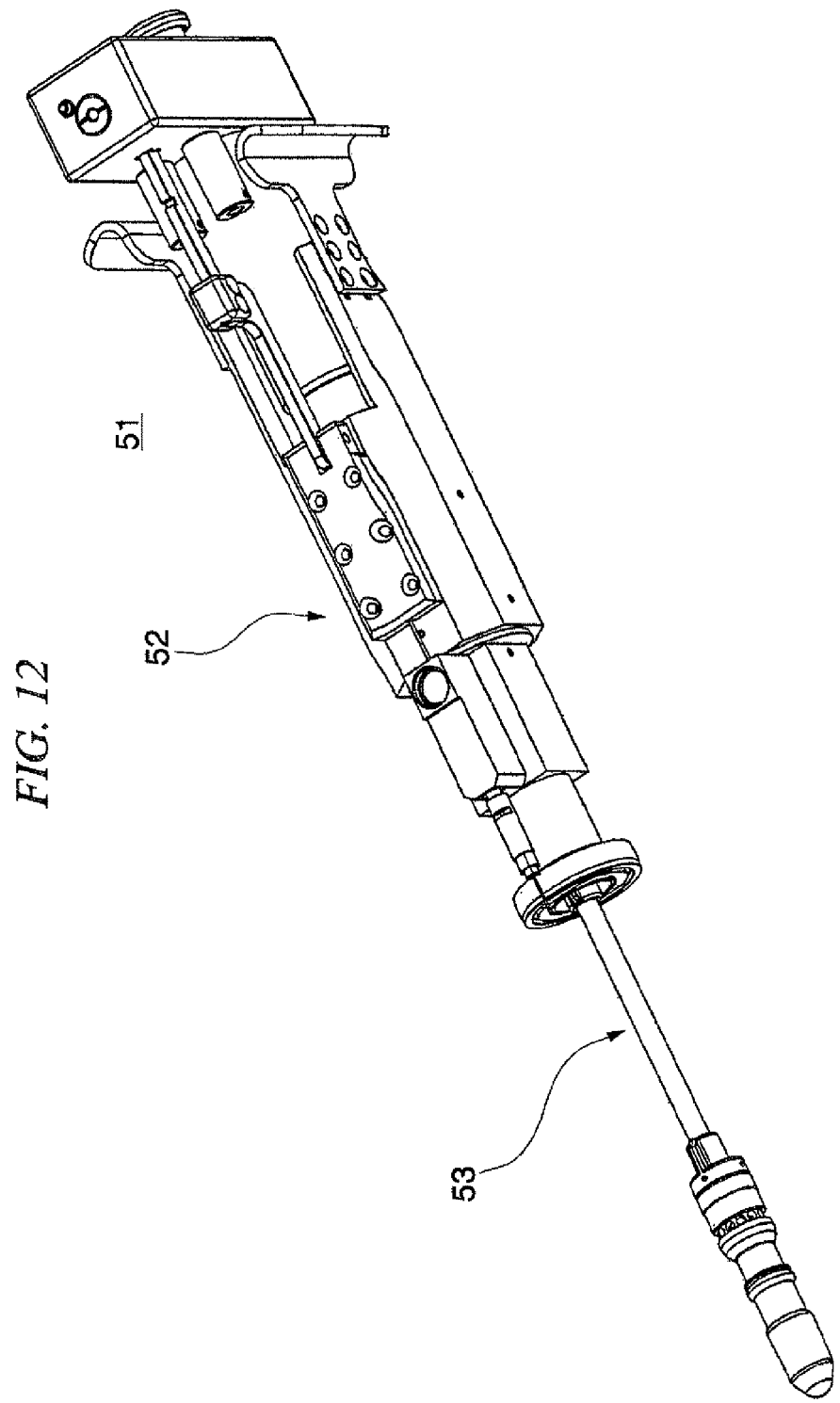
FIG. 12 is an isometric view of an operation stick of the first operation section of the treatment endoscope according to the second embodiment of the present invention.
Figure 13:
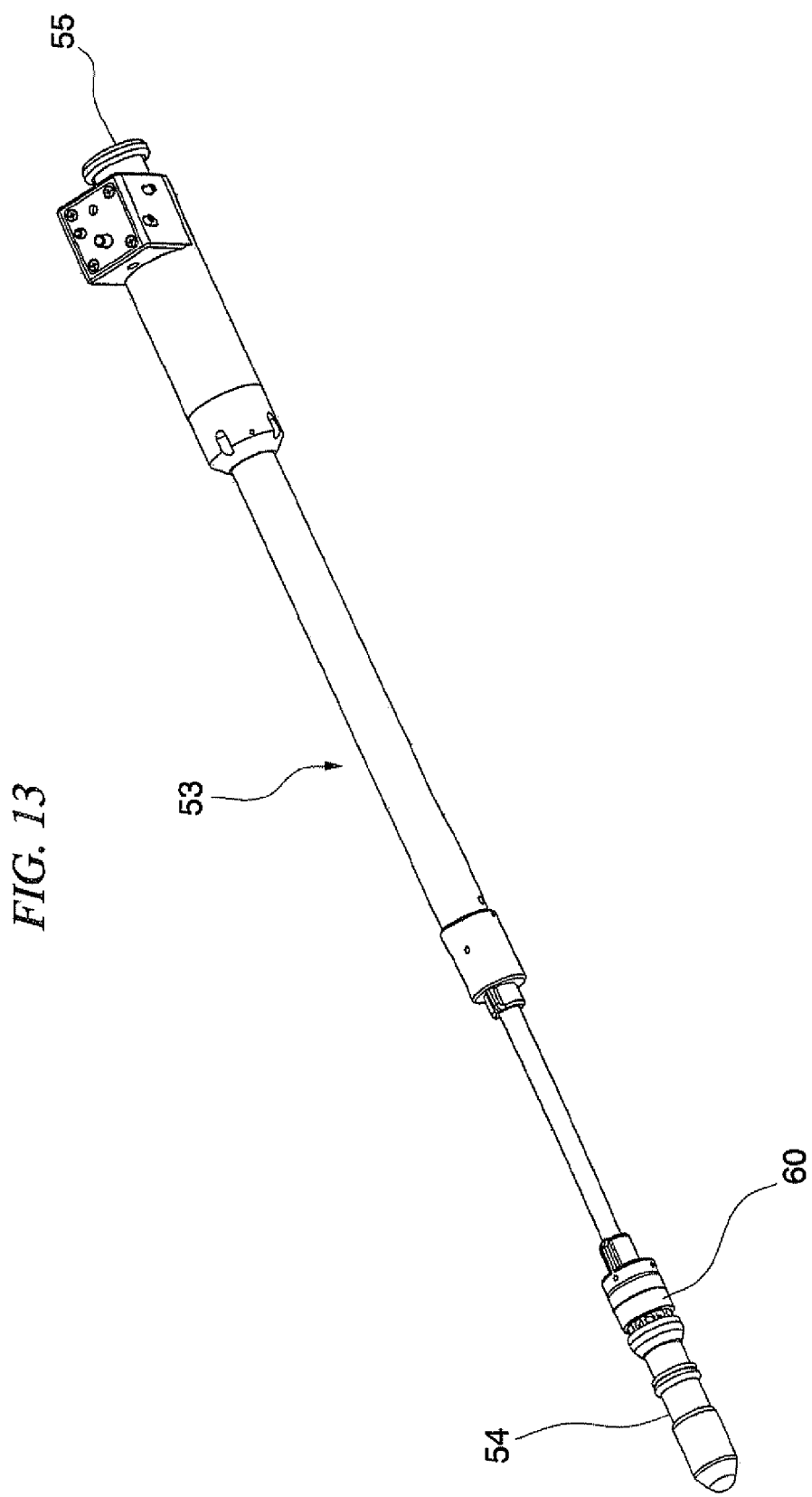
FIG. 13 is an isometric view of a channel unit inserted into the operation stick.

FIG. 12 is an isometric view of an operation stick 52 attached to the first operation section of a treatment endoscope 51 according to the present embodiment. The operation stick 52 having substantially the same structure as that disclosed in U.S. patent application Ser. No. 12/057,990 has a channel unit 53 inserted therethrough detachably as shown in FIG. 13.

The lumen of the channel unit 53 is a channel for allowing a treatment instrument to pass therethrough and to project from the distal ends of the arm section 3. The channel unit 53, except for a part thereof is fully made of stainless steel SUS303 for reuse by conducting cleaning or autoclave sterilization, etc. Stainless steel SUS304 may be used in place of stainless steel SUS303.

A first cap 54 and a second cap 55 for sealing the two ends of the channel and maintaining a sterilized condition in the channel prior to the usage thereof are attached to the channel unit 53. Prior to using the treatment endoscope 51, the channel unit 53 is inserted into the operation stick 52, and the caps 54 and 55 are removed.

Figure 14:
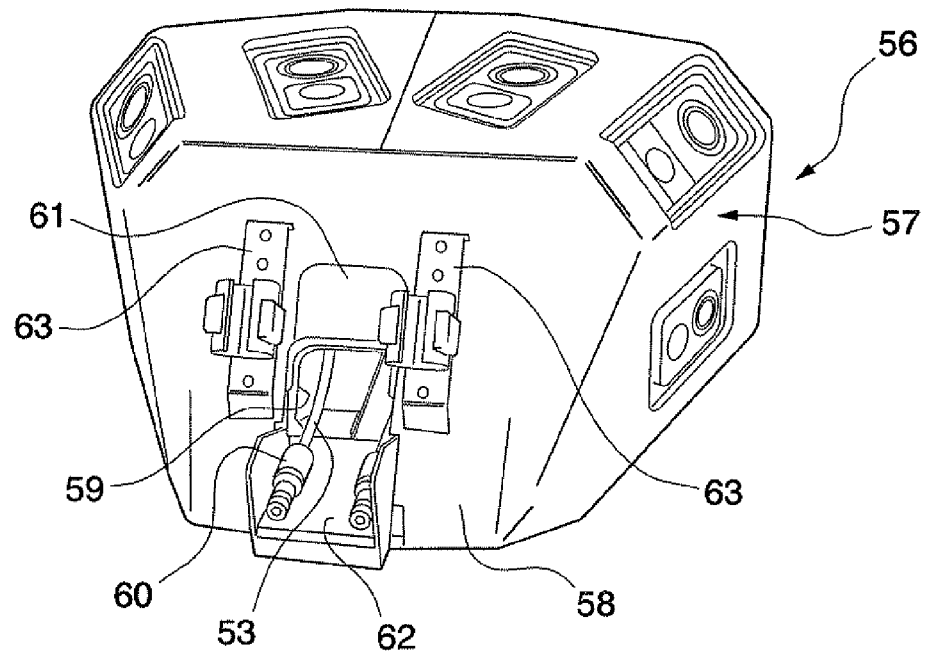
FIG. 14 is an isometric view of the first operation section covered with a cover.

A first operation section 56 having two operation sticks 52 attached thereto is fully covered with a cover 57 as shown in FIG. 14. It should be noted that FIG. 14 omits a first operation shaft and a second operation shaft to render the drawing more legible.

An opening 59 is formed on a front surface 58 of the cover 57 positioned distally relative to the first operation section 56. The distal end of each channel unit 53 inserted through the operation stick 52 projects from the opening 59. A treatment-instrument channel in the insertion section 2 (not shown in the drawing) communicates with the channel formed in the channel unit 53 via a connecting section 60 provided to the distal end of the channel unit 53.

A shutter 61 capable of sliding in a vertical direction is attached to the opening 59. This configuration which does not prevent the movement of the distal end section of the channel unit 53 including the connecting section 60 and shields the opening 59 as much as possible can reliably maintain hygienic condition.

The distal end section of a stage 62 formed substantially parallel with the distal end section of the channel unit 53 projects ahead of the opening 59. The structure of the stage 62 will be later explained in detail. Since the connecting section 60 is disposed on the stage 62, the user can conduct smooth operations by smoothly moving the connecting section 60 on the stage 62.

Figure 15:
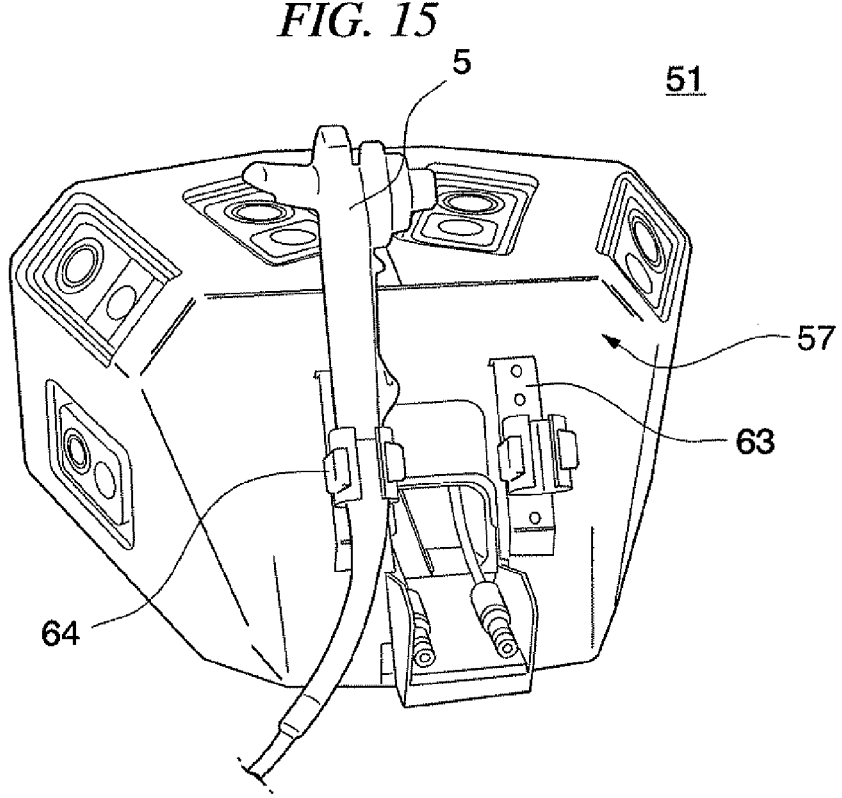
FIG. 15 shows a second operation section maintained by the cover

Holder bases 63 are attached unitarily on two areas lateral to the opening 59 of the front surface 58. A holder 64 for holding the second operation section 5 is attached to each holder base 63 as shown in FIG. 15. Each holder 64 is detachable and capable of moving along the holder base 63 in a fixed range. The holder 64 can be mounted to the holder base 63 over a drape which covers the cover 57 fully surrounding the first operation section 56 for the sake of pollution prevention as disclosed in the U.S. patent application Ser. No. 12/057, 990.

Figure 16:
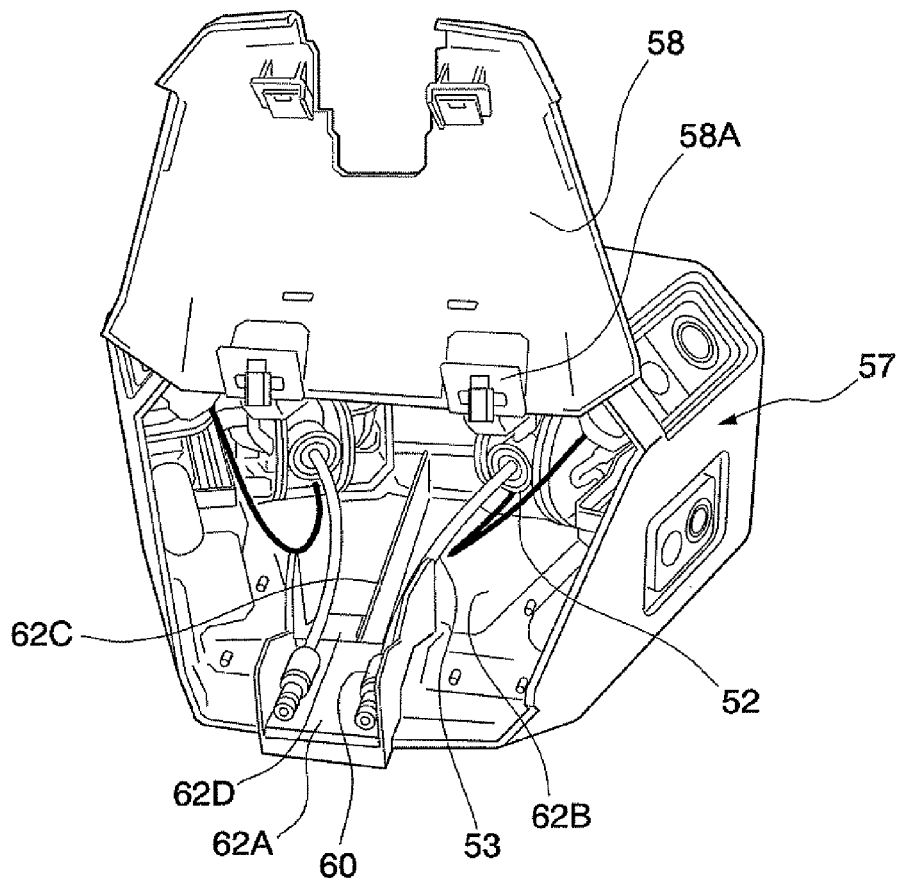
FIG. 16 is an isometric view showing an opening state of the front surface of the cover.

FIG. 16 shows the open state of the front surface 58. The front surface 58 capable of freely opening and closing is connected to the other portion of the cover 57 detachably by hinges 58A provided to the upper section of the front surface 58. In addition, each hinge 58A having a commonly known lock mechanism, which is not shown in the drawings, is configured to be unoperable unless a predetermined value of force is applied in a closed state as shown in FIG. 14 and in an opened state as shown in FIG. 16. Therefore, even if the cover 57 leans, it does not close by the self weight of front surface 58, and the front surface 58 is prevented inadvertently from opening from the closed state of the front surface 58.

The stage 62 has a first stage 62A projecting from the opening 59; a second stage 62B provided proximally relative to the first state 62A; a bulkhead 62C provided in the middle in the width direction of the second stage 62B; and a connecting stage 62D for steplessly connecting the first stage 62A to the second stage 62B. According to the aforementioned configuration, the distal end section of the channel unit 53, which is inserted into the operation stick 52 and includes the connecting section 60, projects from the distal end of the operation stick 52 and father projects above the second stage 62B. Subsequently, the distal end sections upon moving ahead (distally) while sliding on the second stage 62B are guided by the bulkhead 62C and the connecting stage 62D, and moves onto the first stage 62A smoothly and automatically without intersecting as shown in FIG. 16. In the unlikely event that, for example, the distal end section falls off from above the stage 62 in the cover 57, the user can grasp the distal end section directly by opening the front surface 58 and dispose the distal end section on the first stage 62A.

Figure 17:
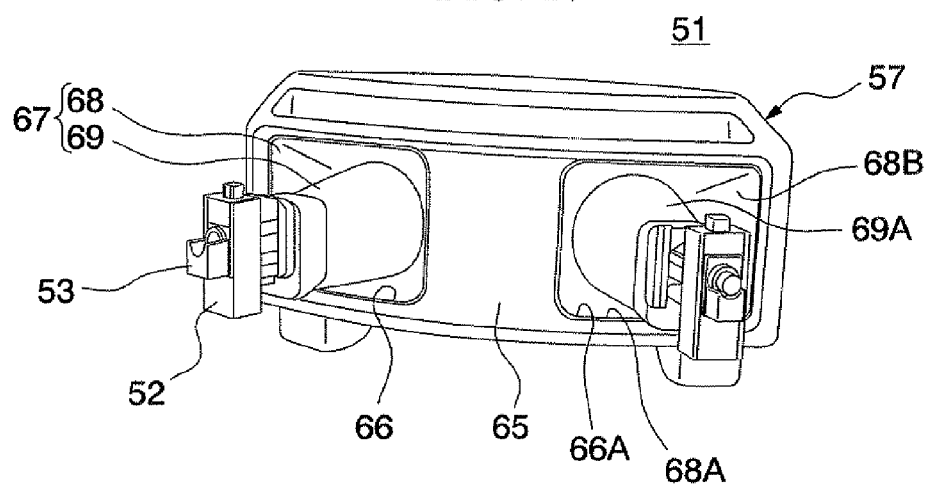
FIG. 17 shows the vicinity of the rear surface of the cover.

FIG. 17 shows a rear surface 65 of the cover 57 disposed proximally relative to the first operation section 56. Two openings 66 are provided on the rear surface 65. The proximal end of the operation stick 52 having the channel unit 53 inserted therethrough projects from each opening 66.

A boot 67 made of an elastic material, e.g., rubber, is attached to each opening 66. The boot 67 includes an outer layer 68 having a substantial four-sided pyramid shape; and a substantially cylindrical inner layer 69. A periphery 68A disposed proximally relative to the outer layer 68 is attached to a periphery 66A of the opening 66 unitarily. The inner layer 69 covers the external surface of the operation stick 52 and the vicinity of a swinging center to which the first operation shaft and the second operation shaft are attached. The distal end section of the inner layer 69 is joined to the distal end section of the outer layer 68. Consequently, the user is prevented from touching each mechanism of the first operation section 56 contained in the cover 57 since the opening 66 is sealed by an inner surface 68B of the outer layer 68 and an outer surface 69A of the inner layer 69.

The treatment endoscope 51 according to the present embodiment can obtain the same effect as that of the treatment endoscope according to the aforementioned each embodiment.

Also, the cover 57 covering the first operation section 56 can hold the second operation section 5 for operating the insertion section 2 via the holder base 63 and the holder 64. Therefore, a more facilitated one-person operation can be provided to the user who operates the first operation section 56 and the second operation section 5.

Furthermore, pollution caused by the user who touches each mechanism of the first operation section 56 in the cover 57 can be desirably prevented since the opening 66 of the rear surface 65 of the cover 57 is sealed by the boot 67.

Also, the easily deformable elastic boot 67 made of a a material having flexibility does not prevent the vertical and horizontal swinging operations of each operation stick 52 along with the operation. Therefore, the user can conduct an operation smoothly.

In addition, although the sealing section of each opening 66 has bumpy portions and recessed portions, each opening 66 free from fine complex shape is formed to have many flat or smooth sections since each opening 66 sealed by two surfaces including the inner surface 68B of the outer layer 68 of the boot 67 and the outer surface 69A of the inner layer 69. Therefore, the sealing section can be cleaned easily, and the maintenance capability can be enhanced.

Although the present invention has been described with respect to its preferred embodiments, the present invention is not limited to the embodiments described above. The configuration of the present invention allows for addition, omission, substitution and further modification without departing from the spirit and scope of the present invention.

For example, the aforementioned each embodiment explained with reference to the example in which the first operation section and the second operation section makes linked movements when either one of them is operated can be replaced by an endoscope having a configuration in which a commonly known one-way clutch is attached to one of the two components so that the two components make linked movements only when the predetermined first operation section or the second operation section is operated. This can provide a treatment endoscope having a configuration capable of corresponding to more complex operations.

Also, the aforementioned each embodiment explained with reference to the example in which the arm section 3 and the insertion section 2 make linked bending movements by operating the two laterally aligned arms of the arm section can be replaced by a treatment endoscope having a configuration in which, the two components make bending movements linked with bending movement in other directions, for example, in the rising-and-falling direction relative to FIG. 11.

The linked bending directions of the arm section and the insertion section may be set desirably in accordance with manipulation conducted to a treatment site. It should be noted that treatment, etc. can be progressed while changing the direction of linked movement in accordance with the detail of manipulation by rendering the interlock mechanism including the link pulleys and the link wires freely detachable with respect to each operation shaft.

Furthermore, the aforementioned embodiments explained with reference to the example in which the interlock mechanism uses wires and link pulleys in configuration can be replaced by other commonly known configurations, for example, using chains and sprockets that makes linked movements, or a rack-and-pinion mechanism in which the proximal ends of wires are fixed to a rack to make linked movements.

In addition, the number of arms is not limited specifically to the aforementioned each embodiment explained with reference to the example in which two arms are attached to the distal end of the insertion section. That is, the arm may be in a single piece, or in three or more pieces. Also, the insertion section and the arm may not have an operation channel, and a treatment mechanism such as a grasping forceps may be attached to the distal end of the arm.

Also, an observation device 72 in an initial state attached to the distal end of the insertion section may be positioned below the two arm sections 3A and 3B similarly to a treatment endoscope 71 according to a modified example shown in FIG. 18A. In this configuration, the proximal end of the arm section 3 can be projected in the upper region of a visual field in the observation device 72 as shown in FIG. 18B. The treatment site and the distal end of the treatment instrument 100 projecting from the arm section 3 can be observed more desirably in the aforementioned modified example in contrast to uneasy observation for a treatment site, etc. with a conventional observation device positioned above the arm sections 3A and 3B and increasing the ratio of the image of the arm sections to the visual field of the observation device.

Figure 19A:
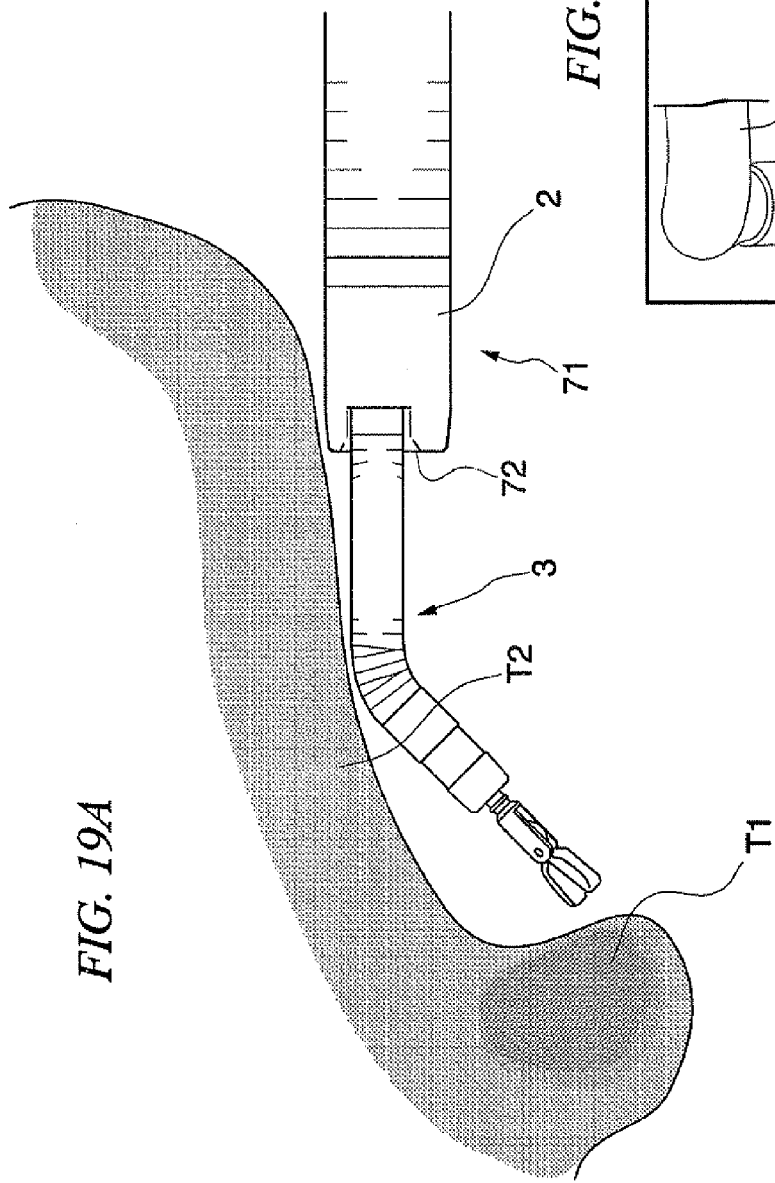
FIG. 19A shows an example of manipulation using the treatment endoscope.

Furthermore, the user conducts manipulation to a treatment-object site T1 existing below a non-treatment-object site T2 as shown in FIG. 19A, which is not treated, by sinking the insertion section 2 under the non-treatment-object site T2, raising the non-treatment-object site T2 by operating the arm section 3, and rendering the treatment-object site T1 observable.

Figure 19B:
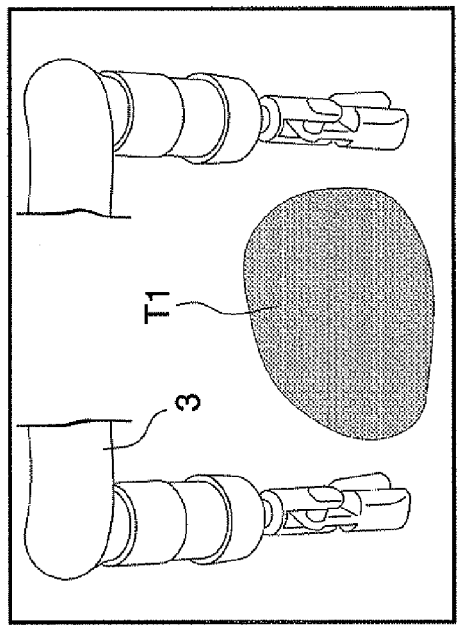
FIG. 19B shows a visual field of the observation device of the treatment endoscope shown in FIG. 19A.

FIG. 19B shows the visual field in the observation device 72 obtained by pushing the non-treatment-object site T2 upwardly with the arm section 3. The visual field is not blocked since the non-treatment-object site T2 is positioned above the arm section 3; therefore, the treatment-object site T1 can be observed desirably since the arm section 3 is positioned upward. Consequently, the user can conduct manipulation easily. In the conventional case in which the observation device is disposed above the arm section, the arm section must be raised above the observation device to push the non-treatment-object site T2 above the observation device. However, it is difficult to conduct manipulation while maintaining such state.

The present invention is not limited to the above descriptions but is limited only by the appended claims.

What is claimed is:

1. A treatment endoscope, comprising:
an insertion section elongated along a longitudinal axis;
an arm section;
a first bending section which is capable of being bent, disposed on the arm section;
a second bending section which is capable of being bent, disposed on a distal end of the insertion section, wherein the arm section is attached to a distal end of the second bending section;
a first rotating member configured to make the first bending section bent, which is capable of rotating around a predetermined rotation axis and has a first outer surface perpendicular to the predetermined rotation axis;

a second rotating member configured to make the second bending section bent, which is capable of rotating around the predetermined rotation axis and has a second outer surface approximately parallel to the first outer surface;

a first operation section for rotating the first rotating member so that the first bending section bends;

a second operation section for rotating the second rotating member so that the second bending section bends; and an interlock mechanism which is capable of switching between an unlinked state and a linked state, wherein the unlinked state is that the second rotating member is capable of rotating with respect to the first rotating member by means of the first outer surface and the second outer surface being separated from each other so that the second bending section bends independently of the first bending section by operating the second operation section, and the linked state is that the second rotating member rotates by a friction force acting on between the first outer surface and the second outer surface corresponding to a torque generated by the first rotating member rotating by operating the first operation section by means of the first outer surface and the second outer surface being in contact with each other so that the first bending section bends with the second bending section bending by operating the first operation section.

2. The treatment endoscope according to claim 1, wherein the interlock mechanism comprises a link shaft whose outer periphery has a groove, and the unlinked state and the linked state of the interlock mechanism are able to be switched by operating the first operation section.

* * * * *